(12) United States Patent
O'Brien et al.

(10) Patent No.: US 12,070,228 B2
(45) Date of Patent: Aug. 27, 2024

(54) METHODS OF CONSTRUCTING HEMOSTASIS DEVICES WITH FOLDED BALLOON ASSEMBLIES

(71) Applicant: TERUMO KABUSHIKI KAISHA, Tokyo (JP)

(72) Inventors: Victoria Moore O'Brien, Sewell, NJ (US); Brian Hoffman, Princeton, NJ (US); Kenichi Hazama, Bear, DE (US); Nicholas Varamo, Hockessin, DE (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 388 days.

(21) Appl. No.: 17/424,929

(22) PCT Filed: Feb. 28, 2020

(86) PCT No.: PCT/US2020/020500
§ 371 (c)(1),
(2) Date: Jul. 22, 2021

(87) PCT Pub. No.: WO2020/180731
PCT Pub. Date: Sep. 10, 2020

(65) Prior Publication Data
US 2022/0087689 A1 Mar. 24, 2022

Related U.S. Application Data

(60) Provisional application No. 62/812,436, filed on Mar. 1, 2019.

(51) Int. Cl.
*A61B 17/135* (2006.01)
*A61B 17/132* (2006.01)
(Continued)

(52) U.S. Cl.
CPC ........ *A61B 17/135* (2013.01); *A61B 17/1325* (2013.01); *A61B 2017/00526* (2013.01);
(Continued)

(58) Field of Classification Search
CPC .............. A61B 17/135; A61B 17/1325; A61B 17/1322; A61B 17/1355;
(Continued)

(56) References Cited

U.S. PATENT DOCUMENTS 5,588,956 A * 12/1996 Billotti .................... A61F 5/012
128/DIG. 20
5,783,227 A 7/1998 Dunham
(Continued)

FOREIGN PATENT DOCUMENTS

| CN | 101453936 A | 6/2009 |
| CN | 203182968 U | 9/2013 |

(Continued)

OTHER PUBLICATIONS

International Search Report (PCT/ISA/210) and Written Opinion (PCT/ISA/237) mailed on Jul. 2, 2020, by the Korean Intellectual Property Office as the International Searching Authority for counterpart International Application No. PCT/US2020/020500.
(Continued)

*Primary Examiner* — John L Goff, II
(74) *Attorney, Agent, or Firm* — BUCHANAN INGERSOLL & ROONEY PC

(57) ABSTRACT

The present application discloses various methods of constructing hemostasis devices with folded balloon assemblies.

20 Claims, 13 Drawing Sheets

(51) Int. Cl.
  *A61B 17/00* (2006.01)
  *A61B 17/12* (2006.01)
  *A61M 39/10* (2006.01)
(52) U.S. Cl.
  CPC .............. *A61B 2017/12004* (2013.01); *A61M 2039/1094* (2013.01)
(58) Field of Classification Search
  CPC ........... A61B 2017/00526; A61B 2017/12004; A61B 2017/00907; A61B 2090/0807; A61B 5/022; A61M 2039/1094; A61F 5/34
  USPC ......................................................... 602/13
  See application file for complete search history.

(56) References Cited

U.S. PATENT DOCUMENTS

| | | | |
|---|---|---|---|
| 7,296,313 B2 * | 11/2007 | Hense | A41D 13/065 128/882 |
| 9,393,027 B1 | 7/2016 | Dooley | |
| 2009/0082626 A1 | 3/2009 | Ichimura et al. | |
| 2018/0028195 A1 | 2/2018 | Benz et al. | |
| 2018/0042615 A1 | 2/2018 | Kimura et al. | |
| 2018/0263634 A1 | 9/2018 | Hoskins et al. | |
| 2018/0310944 A1 | 11/2018 | Benz et al. | |
| 2019/0015100 A1 | 1/2019 | Yigit et al. | |
| 2019/0015110 A1 | 1/2019 | Pancholy et al. | |
| 2019/0021742 A1 | 1/2019 | Hazama | |

FOREIGN PATENT DOCUMENTS

| | | |
|---|---|---|
| CN | 109069163 A | 12/2018 |
| WO | 2006/133539 A1 | 12/2006 |
| WO | 2016/112342 A1 | 7/2016 |
| WO | 2017/165108 A1 | 9/2017 |
| WO | 2018008600 A1 | 1/2018 |

OTHER PUBLICATIONS

The extended European Search Report issued Oct. 21, 2022, by the European Patent Office in corresponding European Patent Application No. 20767421.9-1122. (9 pages).

Office Action (Notification of the First Office Action) issued Mar. 31, 2023, by the National Intellectual Property Administration, P. R. China in corresponding Chinese Patent Application No. 202080017753.7 and an English translation of the Office Action. (20 pages).

Office Action (Notice of Reasons for Refusal) issued May 9, 2023, by the Japan Patent Office in corresponding Japanese Patent Application No. 2021-549783 and an English translation of the Office Action. (18 pages).

Office Action (Notification of The Second Office Action) issued Oct. 19, 2023, by the National Intellectual Property Administration, P. R. China in corresponding Chinese Patent Application No. 202080017753.7 and an English translation of the Office Action. (19 pages).

Office Action (Notification of the Third Office Action) issued on Mar. 4, 2024, in corresponding Chinese Patent Application No. 202080017753.7 and English translation of the Office Action. (16 pages).

* cited by examiner

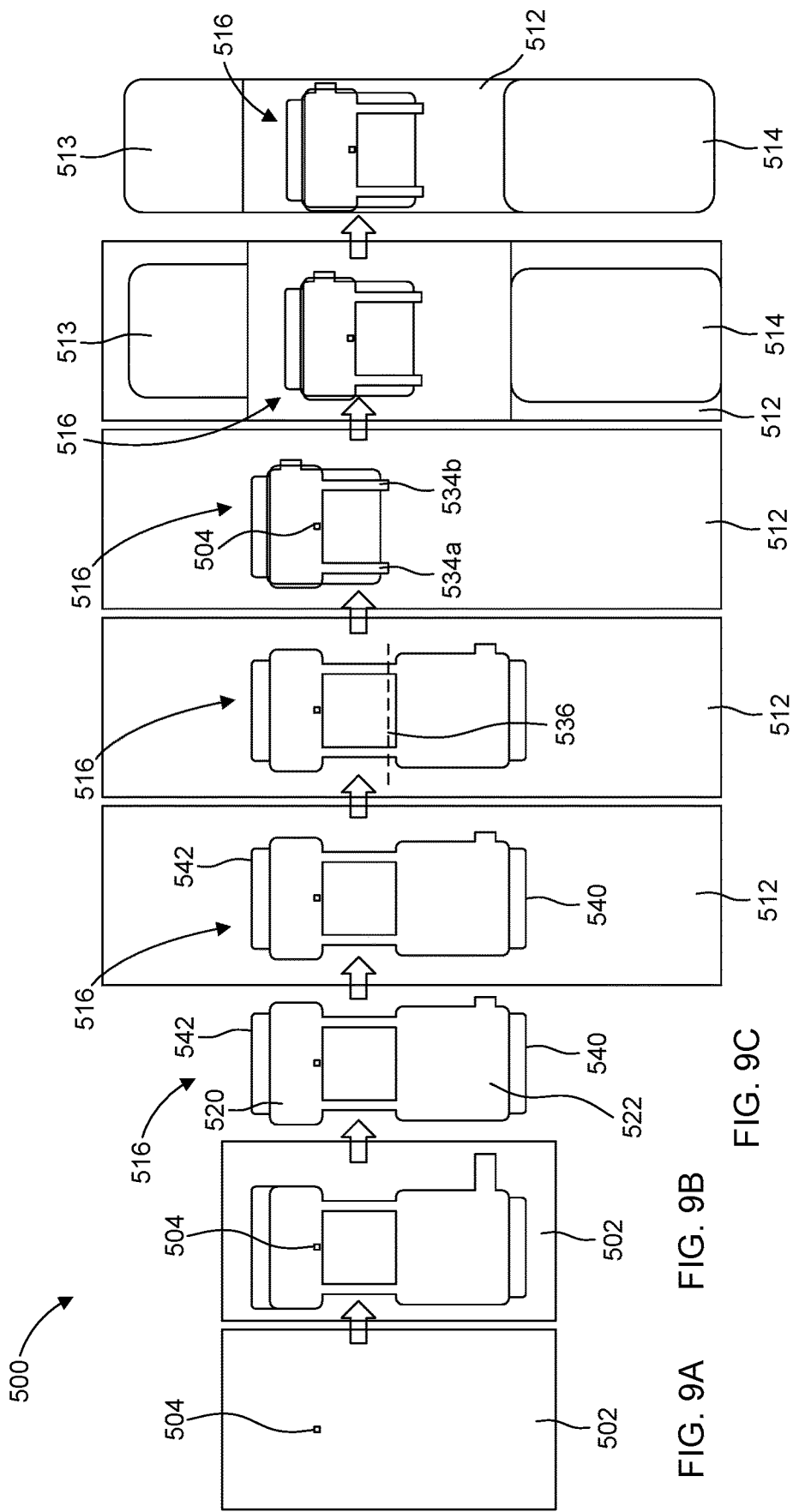

METHODS OF CONSTRUCTING HEMOSTASIS DEVICES WITH FOLDED BALLOON ASSEMBLIES

CROSS-REFERENCE TO RELATED APPLICATION(S)

This application claims priority to U.S. Provisional Patent Application No. 62/812,436, filed Mar. 1, 2019, which is incorporated by reference herein in its entirety.

FIELD OF THE DISCLOSURE

The present disclosure relates to methods of constructing hemostasis devices (e.g., bands) that are adapted to act as compression devices to promote hemostasis at a surgical access site, and more particularly to methods of constructing such devices having folded balloon assemblies.

BACKGROUND

After a surgical procedure involving arterial or venous access, it may be desirable or necessary to apply pressure to the vascular access site to promote hemostasis. Some existing hemostasis devices use one or more inflatable balloons to apply pressure to the access site. In some instances, these balloons have experienced failures. Some existing methods of constructing hemostasis devices are also time-consuming and expensive. Accordingly, there is a need for improved methods that address these and other drawbacks of the prior art.

SUMMARY OF THE DISCLOSURE

In one respect, the present disclosure comprises a method of constructing a hemostasis device, the method comprising: forming a balloon assembly by attaching a top layer of material, a bottom layer of material, and at least one intermediate layer of material together about a perimeter to form at least a portion of a first chamber, the first chamber being inflatable, the at least one intermediate layer creating a gap between the top layer of material and the bottom layer of material adjacent to the perimeter; and connecting the balloon assembly to a flexible band that is attachable around a body part of a patient.

In another respect, the present disclosure comprises a method of constructing a balloon assembly for a hemostasis device, the method comprising: depositing a first layer of glue onto a first layer of material; curing the first layer of glue to form a perimeter, the perimeter forming at least a portion of an outline of a first chamber, at least a portion of an outline of a second chamber, and at least a portion of an outline of at least one channel that is connected between the first chamber and the second chamber; depositing a second layer of glue onto the first layer of material exterior to the perimeter; placing a second layer of material on top of the second layer of glue and the first layer of material; and curing the second layer of glue to attach the second layer of material to the first layer of material and form a contiguous chamber comprising the first chamber, the second chamber, and the at least one channel.

In yet another respect, the present disclosure comprises a method of constructing a balloon assembly for a hemostasis device, the method comprising: attaching a first layer of material to a second layer of material about a perimeter, the perimeter defining at least a portion of a first chamber, at least a portion of a second chamber, and at least a portion of at least one channel, the at least one channel being in fluid flow communication between the first chamber and the second chamber, the first chamber, second chamber, and at least one channel forming a contiguous chamber; and locating at least a portion of the first chamber such that it overlays at least a portion of the second chamber and such that the at least one channel is folded.

FURTHER ASPECTS OF THE INVENTIVE CONCEPT(S)

Further aspects of the inventive concept(s) include:

Aspect 1: A method of constructing a hemostasis device, the method comprising: forming a balloon assembly by attaching a top layer of material, a bottom layer of material, and at least one intermediate layer of material together about a perimeter to form at least a portion of a first chamber, the first chamber being inflatable, the at least one intermediate layer creating a gap between the top layer of material and the bottom layer of material adjacent to the perimeter; and connecting the balloon assembly to a flexible band that is attachable around a body part of a patient.

Aspect 2: The method of Aspect 1, the forming step further comprising attaching the top layer of material, the bottom layer of material, and the at least one intermediate layer of material together about the perimeter to form the at least a portion of a first chamber, at least a portion of a second chamber, and at least a portion of at least one channel, the at least one channel being in fluid flow communication between the first chamber and the second chamber, the first chamber, second chamber, and at least one channel forming a contiguous chamber; the method further comprising locating at least a portion of the first chamber such that it overlays at least a portion of the second chamber and such that the at least one channel is folded.

Aspect 3: The method of Aspect 2, wherein the locating step further comprises folding the at least one channel such that a first portion of the at least one channel overlays a second portion of the at least one channel.

Aspect 4: The method of either of Aspect 1 or Aspect 2, wherein the forming step further comprises attaching the top layer of material, the bottom layer of material, and the least one intermediate layer of material together about the perimeter such that at least one space is left in the perimeter, the method further comprising attaching at least one port through the at least one space such that a fluid may be introduced into the first chamber via the at least one port.

Aspect 5: The method of any of Aspects 2-4, further comprising: prior to completion of the forming step, placing at least one piece of secondary material within the at least one channel.

Aspect 6: The method of Aspect 5, wherein the step of placing at least one piece of secondary material within the at least one channel comprises placing at least one piece of gas-permeable secondary material within the at least one channel.

Aspect 7: The method of Aspect 5, wherein the step of placing at least one piece of secondary material within the at least one channel comprises placing at least one piece of gas-impermeable secondary material within the at least one channel.

Aspect 8: The method of Aspect 5, wherein the step of placing at least one piece of secondary material within the at least one channel comprises placing at least one piece of secondary material within the at least one channel which has a circular cross-sectional shape.

Aspect 9: The method of any of Aspects 2-8, wherein the locating step comprises folding the at least one channel in half.

Aspect 10: The method of any of Aspects 2-8, wherein the forming step further comprises forming a first air channel and a second air channel between the first chamber and the second chamber.

Aspect 11: The method of any of Aspects 2-8, wherein the forming step further comprises attaching the top layer of material, the bottom layer of material, and the at least one intermediate layer of material together about the perimeter to form an outer perimeter, the method further comprising attaching at least the top layer of material and the bottom layer of material together to form an inner perimeter, the inner perimeter being located interior to the outer perimeter.

Aspect 12: The method of Aspect 11, further comprising the step of cutting and removing at least a portion of the top layer of material that is located interior to the inner perimeter and at least a portion of the bottom layer of material that is located interior to the inner perimeter.

Aspect 13: The method of either of Aspect 11 or Aspect 12, wherein the step of attaching at least the top layer of material and the bottom layer of material together to form an inner perimeter further comprises omitting at least a portion of the top layer of material that is located interior to the inner perimeter and at least a portion of the bottom layer of material that is located interior to the inner perimeter.

Aspect 14: The method of any of Aspects 2-13, wherein the forming step further comprises attaching the top layer of material to the bottom layer of material about the perimeter such that the perimeter defines the entireties of the first chamber, the second chamber, and the at least one channel.

Aspect 15: The method of any of Aspects 1-14, wherein the forming step is accomplished using a laser welding process.

Aspect 16: The method of any of Aspects 1-14, wherein the forming step is accomplished using a radio frequency welding process.

Aspect 17: The method of any of Aspects 1-14, wherein the forming step is accomplished using gluing or bonding.

Aspect 18: The method of any of Aspects 1-17, wherein the step of forming a balloon assembly by attaching a top layer of material, a bottom layer of material, and at least one intermediate layer of material together about a perimeter to form at least a portion of a first chamber further comprises using the same type of material for each of the top layer of material, the bottom layer of material, and the at least one intermediate layer of material.

Aspect 19: The method of any of Aspects 1-18, wherein the step of forming a balloon assembly by attaching a top layer of material, a bottom layer of material, and at least one intermediate layer of material together about a perimeter to form at least a portion of a first chamber further comprises using the same type of material for each of the top layer of material and the bottom layer of material, but a different type of material for the at least one intermediate layer of material.

Aspect 20: A method of constructing a balloon assembly for a hemostasis device, the method comprising: depositing a first layer of glue onto a first layer of material; curing the first layer of glue to form a perimeter, the perimeter forming at least a portion of an outline of a first chamber, at least a portion of an outline of a second chamber, and at least a portion of an outline of at least one channel that is connected between the first chamber and the second chamber; depositing a second layer of glue onto the first layer of material exterior to the perimeter; placing a second layer of material on top of the second layer of glue and the first layer of material; and curing the second layer of glue to attach the second layer of material to the first layer of material and form a contiguous chamber comprising the first chamber, the second chamber, and the at least one channel.

Aspect 21: The method of Aspect 20, further comprising the step of inserting a first end of a piece of connection tubing into an interior of the contiguous chamber while leaving a second end of the piece of connection tubing exterior to the contiguous chamber.

Aspect 22: The method of either of Aspect 20 or Aspect 21, further comprising the step of locating at least a portion of the first chamber such that it overlays at least a portion of the second chamber and such that the at least one channel is folded.

Aspect 23: The method of Aspect 22, wherein the locating step further comprises folding the at least one channel such that a first portion of the at least one channel overlays a second portion of the at least one channel.

Aspect 24: A method of constructing a balloon assembly for a hemostasis device, the method comprising: attaching a first layer of material to a second layer of material about a perimeter, the perimeter defining at least a portion of a first chamber, at least a portion of a second chamber, and at least a portion of at least one channel, the at least one channel being in fluid flow communication between the first chamber and the second chamber, the first chamber, second chamber, and at least one channel forming a contiguous chamber; and locating at least a portion of the first chamber such that it overlays at least a portion of the second chamber and such that the at least one channel is folded.

Aspect 25: The method of Aspect 24, wherein the locating step further comprises folding the at least one channel such that a first portion of the at least one channel overlays a second portion of the at least one channel.

Aspect 26: The method of either of Aspect 24 or Aspect 25, wherein the attaching step further comprises attaching the first layer of material to the second layer of material about the perimeter such that at least one gap is left in the perimeter, the method further comprising attaching at least one port through the at least one gap such that a fluid may be introduced into the contiguous chamber via the at least one port.

Aspect 27: The method of any of Aspects 24-26, further comprising: prior to completion of the attaching step, placing at least one piece of secondary material within the at least one channel.

BRIEF DESCRIPTION OF THE DRAWINGS

The present disclosure will hereinafter be described in conjunction with the appended drawing figures, wherein like numerals denote like elements.

FIGS. 9A-9H show steps of a method of constructing a hemostasis device including a folded balloon assembly in accordance with the present disclosure;

DETAILED DESCRIPTION OF THE EMBODIMENT(S)

Figure 1:
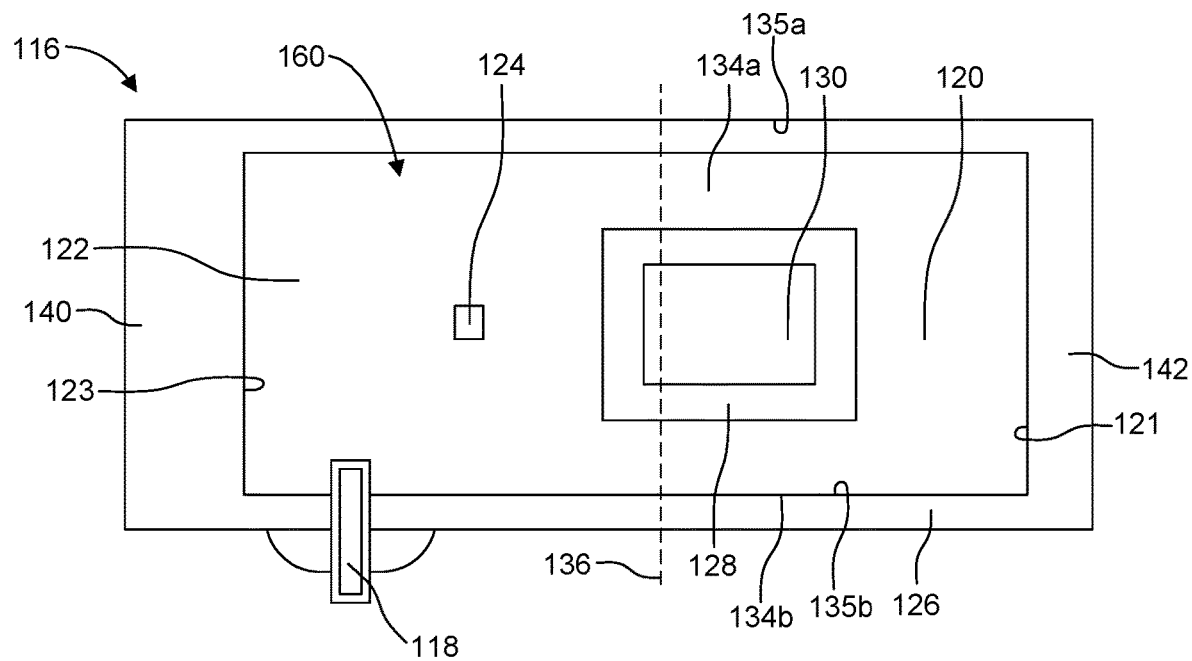
FIG. 1 is a schematic top view of a balloon assembly constructed using a method according to the present disclosure, shown unfolded while in an uninflated state.

The ensuing detailed description provides exemplary embodiment(s) only, and is not intended to limit the scope, applicability, or configuration thereof. Rather, the ensuing detailed description of the exemplary embodiment(s) will provide those skilled in the art with an enabling description for implementing these embodiment(s). It should be understood that various changes may be made in the function and arrangement of elements of the embodiment(s) without departing from the spirit and scope of the invention, as set forth in the appended claims.

Directional terms (e.g., upper, lower, left, right, etc.) may be used herein. These directional terms are merely intended to assist in disclosing the embodiment(s) and claiming the invention and are not intended to limit the claimed invention in any way. In addition, reference numerals that are introduced in the specification in association with a drawing figure may be repeated in one or more subsequent figure(s) without additional description in the specification, in order to provide context for other features. Unless specified, the specific order of step(s) recited in any method claim do not form a limitation of said claim.

Peripheral vascular interventions are commonly used to attempt to clear occlusions from, or surgically introduce stents into, vascular pathways. For example, antegrade crossing via the radial artery in a patient's wrist is common, and various retrograde approaches upwardly from below a patient's knee are also established procedures. After such a procedure, the vascular (i.e., either arterial or venous) access site is typically closed through application of pressure to encourage hemostasis.

Hemostasis devices that are wrapped around a patient's limb at a site on the limb where bleeding is to be stopped, and which include one or more inflatable balloons or bladders that target pressure at a vascular access site, are known in the art. Multiple embodiments of one such hemostasis device and methods of using such devices are described in U.S. Pat. No. 7,498,477, the entirety of which is incorporated by reference as if set forth herein. Additional embodiments of such hemostasis devices and methods of using same are described in U.S. patent application Ser. No. 16/288,303, filed Feb. 28, 2019, the entirety of which is incorporated by reference as if set forth herein. It should be understood that the devices and methods taught herein could be used or adapted for use with any of the hemostasis devices taught in the references noted above in this paragraph.

As discussed in the '477 Patent noted above, such hemostasis devices generally include a rigid member (e.g., a curved plate that slips into a band) and at least one inflatable balloon that, when inflated, expands in a direction away from the rigid member and presses into a targeted location on a patient's limb or other body part, thereby promoting hemostasis. Many of these devices have a dual-balloon design including a connection port that connects the chambers of the two balloons in fluid-flow connection, such that inflating one balloon will cause the fluid (e.g., air) to flow through the connection port and fill the other balloon. These connection ports are typically made via radio frequency ("RF") welding or bonding between faces of the adjacent balloons. In some instances these connection ports can fail, thus causing the balloon assembly of the hemostasis device to fail to properly inflate. The connection port design also requires multiple manufacturing steps and costly and time-consuming manual placement of components during the construction process. Accordingly, there is a need for improved balloon assembly structures and methods of constructing same.

The present disclosure describes various methods of constructing improved balloon assemblies, each of which omit the connection port between the balloons. Several of the methods described herein include the steps of forming two or more balloon chambers and a connecting air channel via connecting two or more layers of material (e.g., vinyl or PVC) together about a single welded perimeter, and then folding the structure about a fold line to form a balloon assembly that includes the small balloon located atop the large balloon, with the folded, integral air channel routed between the two balloons. Said another way, the step of forming the two or more balloon chambers and the air channel that connects between the balloon chambers is done via a single welding or forming step to create a contiguous air chamber that includes the plurality of balloons and the air channel(s) that connect the plurality of balloon(s) together. In an alternative embodiment according to the present disclosure a plurality of balloons are formed separately, a multi-output connector having one air input is formed with inflation tubing split into the appropriate number of output connection tubes (e.g., a "Y"-shaped connector with one input and two outputs), and each of the individual output connection tubes is separately routed into a respective one of the plurality of balloons. In either approach, significantly fewer manufacturing steps are needed, placement of the components of the balloon assembly is simpler and more automatable, and the relatively-weak connection port is eliminated.

Referring now to FIGS. 1-5, one embodiment of a balloon assembly 116 constructed according to a method of the present disclosure will be described in detail. The hemostasis devices shown in the Figures are generally designed to be wrapped and secured in place around the arm of a patient near the wrist to encourage hemostasis of the radial artery, as would be understood by a person having ordinary skill in the art. However, it should be understood that the concepts discussed in the present disclosure have applicability to other hemostasis devices that may be employed elsewhere on a patient's body, for example on any portion of any limb or the torso, neck, or head, and could be used for either arterial or venous hemostasis applications. Further, while it is generally desirable that the balloon assemblies according to the present disclosure be substantially transparent to permit visibility of the vascular access site (both for placement and for monitoring of complications), in alternative embodiments these balloon assemblies be partially or entirely opaque.

Figure 2:
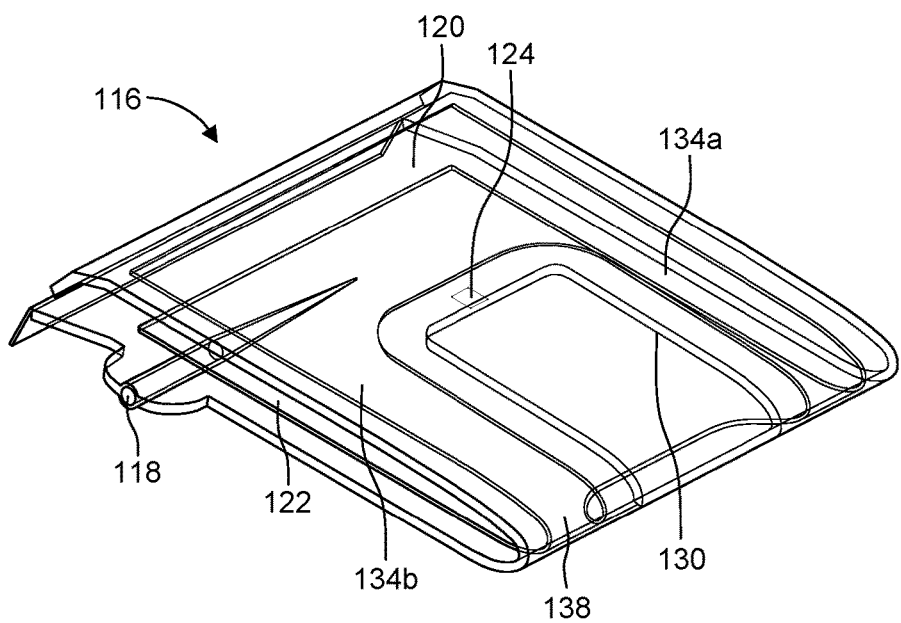
FIG. 2 is a top perspective view of a commercial embodiment thereof, shown folded while in its uninflated state.
Figure 3:
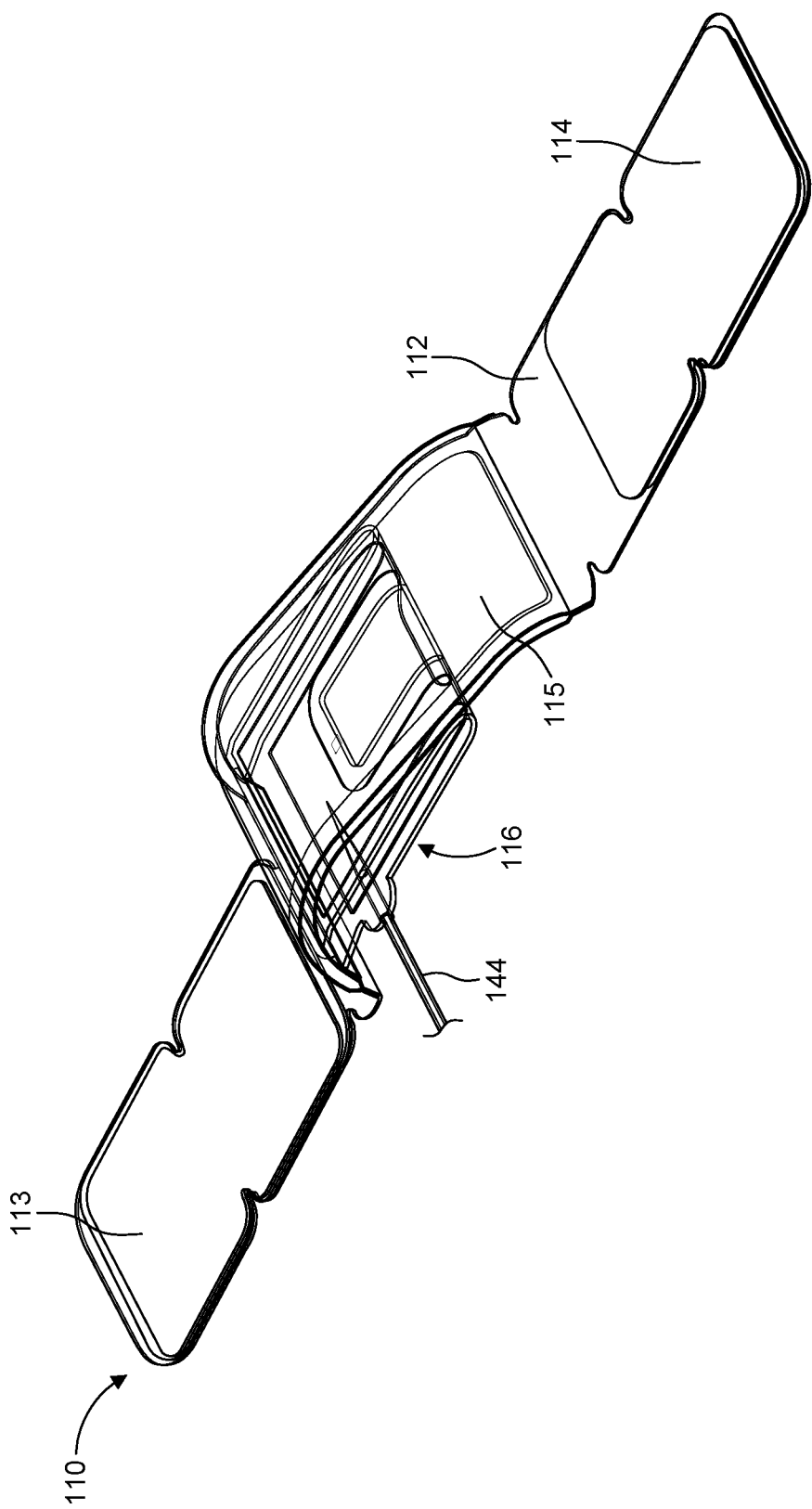
FIG. 3 is a top perspective view of an exemplary hemostasis device, including the folded balloon assembly according to FIG. 2, with the folded balloon assembly shown in an uninflated state.
Figure 4:
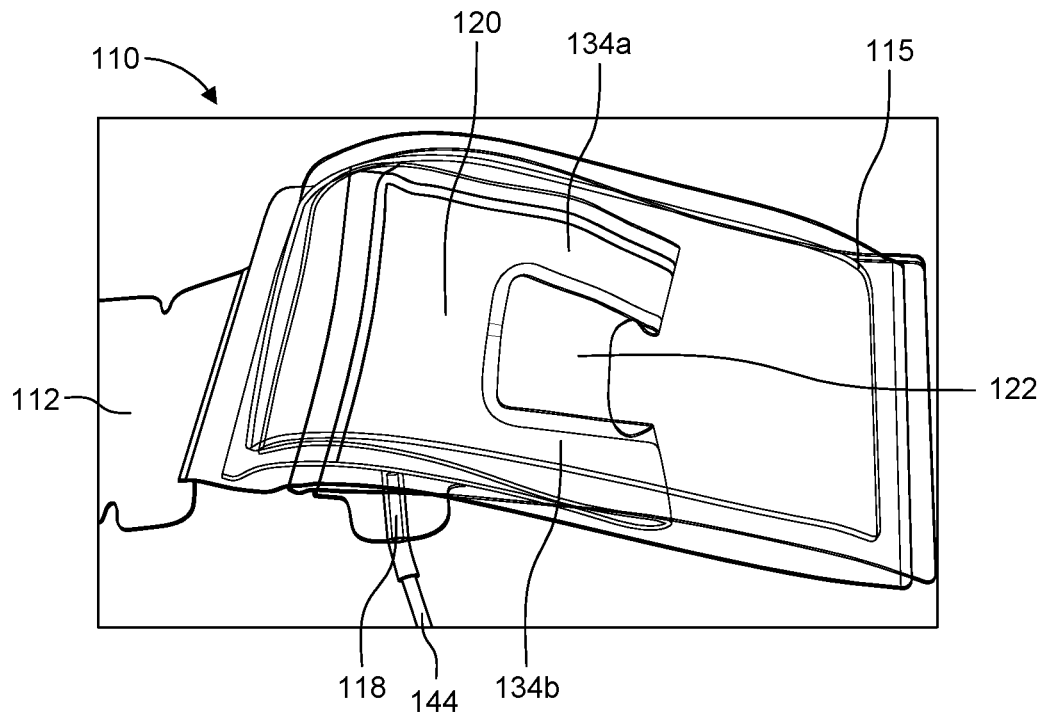
FIG. 4 is a top perspective view thereof, with the folded balloon assembly shown in an inflated state.
Figure 5:
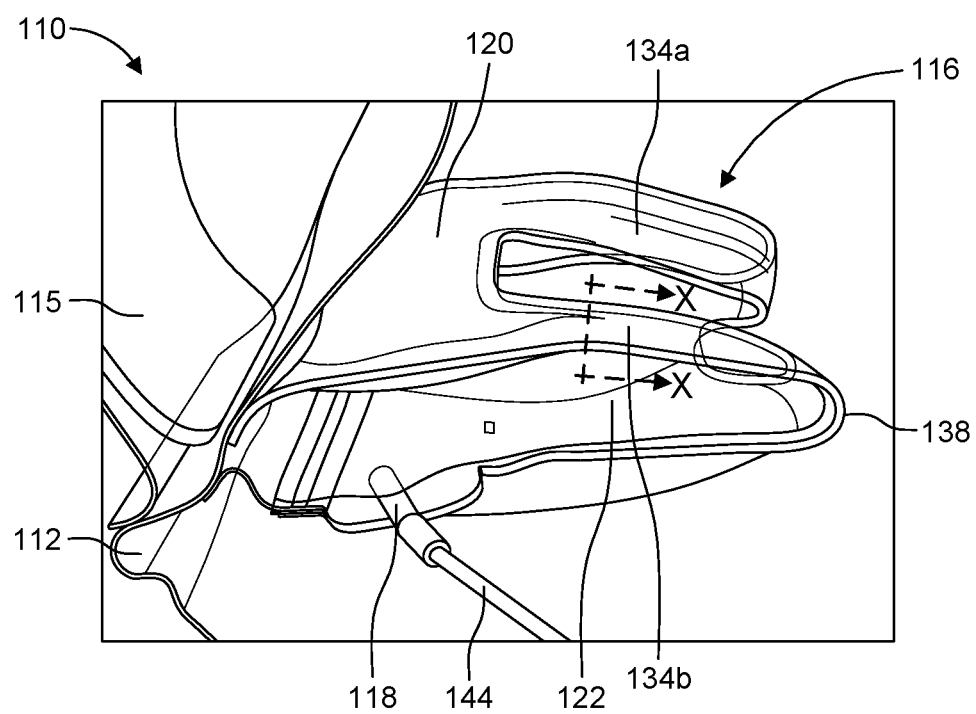
FIG. 5 is a perspective side view thereof.

FIGS. 1 and 2 show various views of a balloon assembly 116 constructed according to a method of the present disclosure, and FIGS. 3-5 show the balloon assembly 116 attached to an exemplary hemostasis device 110. FIGS. 1-5 show a "reverse end-fold" design for a balloon assembly 116 which has a single, welded outer perimeter 126 and a single, welded inner perimeter 128 around which a pair of air channels 134a,134b are formed. In this embodiment, both perimeters 126,128 are formed by laser welding the material layers together, but other construction methods are possible for connecting the material layers of the balloon assembly 116, for example but not limited to RF welding or gluing. In this embodiment, a cutout 130 is made within the inner perimeter 128 after it has been formed so that the channels 134a,134b are separate portions which are located on opposite sides of the cutout 130. In the alternative, the cutout 130 may be omitted so that the inner perimeter 128 surrounds a fully-welded region of two or more layers of material. In the present embodiment, the balloon assembly 116 is fully constructed by being folded about the fold line 136 so that a folded portion 138 is formed that includes the channels 134a,134b, and a small balloon 120 is located atop a large balloon 122. In this and other embodiments according to the present disclosure, placing the balloon assembly 116 in its folded configuration aligns a first portion of the channel 134a atop a second portion of the channel 134a and aligns a first portion of the channel 134b atop a second portion of the channel 134b.

Via a single welding step of forming the two perimeters 126,128, the folded balloon assembly 116 of the present embodiment creates a dual-balloon structure comprising the small balloon 120, the large balloon 122, and the integrated air channels 134a,134b connecting the balloons 120,122, thereby achieving elimination of the weak welded connection port of the prior art devices while reducing the number of steps involved in the construction process. The small balloon 120, the large balloon 122, and the integrated air channels 134a,134b collectively comprise a contiguous air chamber 160, each component of which is formed at least in part by the single welding step. More particularly, the small balloon 120 has a perimeter 121, the large balloon 122 has a perimeter 123, and each of the air channels 134a,134b has a respective perimeter 135a,135b, and at least a portion of each of the perimeters 121,123,135a,135b—specifically, respective outer edge portions of each perimeter 121,123, 135a,135b—is formed by the outer perimeter 126.

Figure 8A:
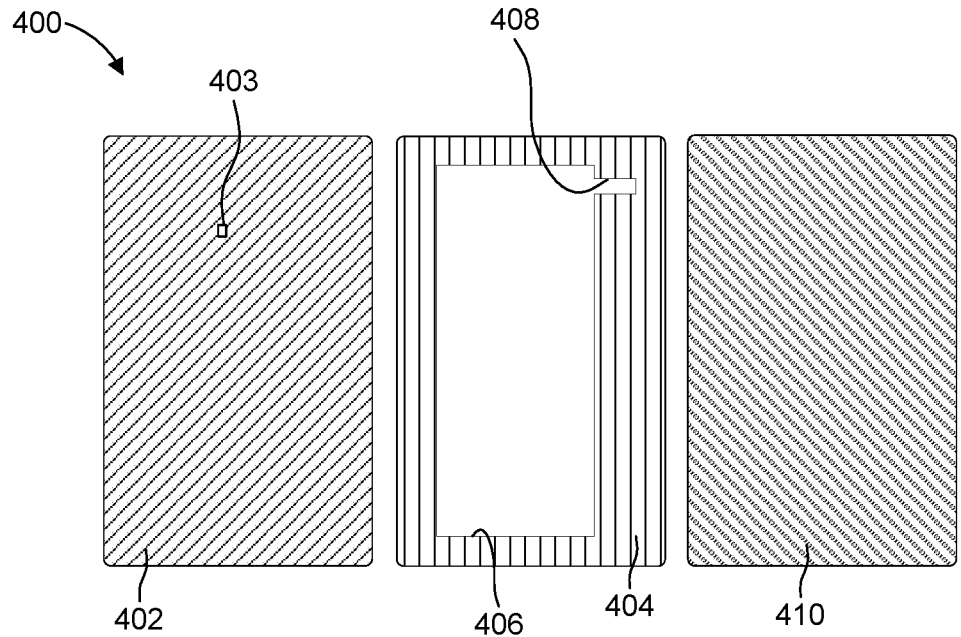
FIGS. 8A-8C show steps of yet another method of constructing a folded balloon assembly in accordance with the present disclosure.
Figure 8B:
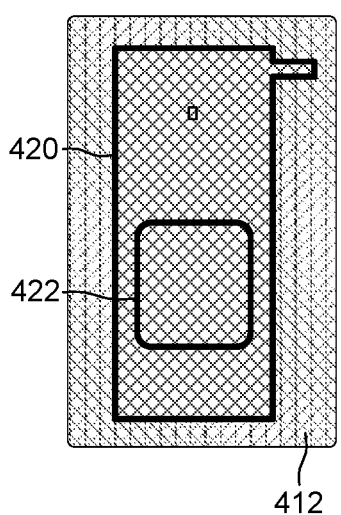
Figure 8C:
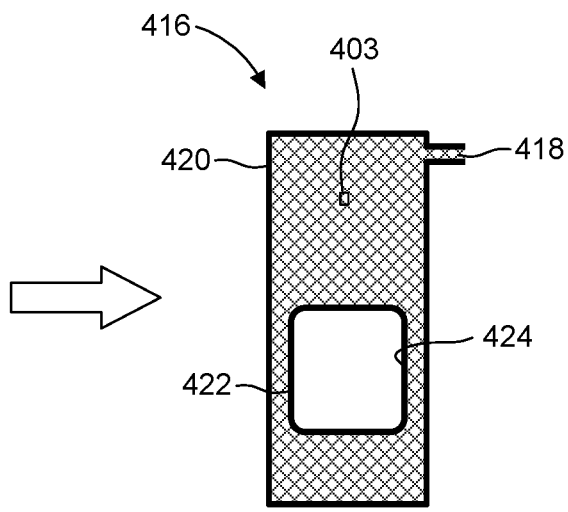

In the embodiment shown in FIGS. 1-5, the balloon assembly 116 is comprised of three layers of material around its outer perimeter 126 and two layers of material around its inner perimeter 128 (see also the balloon assembly formed through the method 400 of FIGS. 8A-8C). In alternative embodiments, the balloon assembly 116 may be formed by attaching any plural number of material layers together about either or both of the outer perimeter 126 and inner perimeter 128, in different combinations, as would be appreciated by a person having ordinary skill in the art.

Turning back to the embodiment of FIGS. 1-5, the balloon assembly 116 is attached to the hemostasis device 110 via two separate attachment hinges 140,142, but in alternative embodiments a reverse end-fold balloon assembly design could have a single, shared attachment hinge by which the balloon assembly is attached to a hemostasis device. Further, while in the present embodiment two air channels 134a, 134b are formed, this type of balloon assembly design could be formed with any number of air channels between the balloons 120,122.

In the present embodiment, the balloon assembly 116 includes an indicator 124 located on the large balloon 122 that is used to help the clinician properly align the hemostasis device 110 on the patient's body part (i.e., adjacent to or atop the vascular access site) before, during, or after inflation of the balloon assembly 116. Omitting a welded connection port from the balloon assembly 116 provides the additional benefit of enhancing the visibility of the indicator 124 and the underlying vascular access site, thereby increasing the likelihood that the clinician will perform the hemostasis procedure accurately. In alternative embodiments, the indicator 124 could be located elsewhere on the balloon assembly 116, located elsewhere on the hemostasis device 110 (e.g., on the flexible band or rigid insert plate), or omitted entirely.

FIGS. 3-5 show the hemostasis device 110 comprising the balloon assembly 116 attached to a band 112 according to the disclosure of U.S. patent application Ser. No. 16/288, 303. The hemostasis device 110 further comprises a rigid insert plate 115 that acts to direct the force of the inflated balloon assembly 116 towards the vascular access site, and complementary fastener patches 113,114 (e.g., of hook-and-loop type, though other fastener types are possible) located on the band 112 that are used to close and secure the band 112 around a patient's body part. In this embodiment, the balloon assembly 116 is inflatable via any suitable connector and valve assembly that is connectable to an inlet 118 of the balloon assembly 116 for introduction of air into the balloon assembly 116 via a connection tubing 144.

While the embodiments discussed herein are designed as two-balloon structures, additional folds or split air lines could be used to form a balloon assembly having any number of balloons or separate air chambers in accordance with the concepts and methods taught herein. Further, in accordance with any of the embodiments, structures, concepts, or methods taught herein, the channel(s) or air passages between the balloons could be of any number, could be of any non-linear shape (e.g., angled, zig-zagged, curved), and/or could split, combine, or both. In alternative embodiments, any connection tubing could be replaced by a "chimney port" or hose barb.

There is some possibility that the folded channel(s) of each balloon assembly constructed according to methods of the present disclosure could become tightly creased when the balloon assembly is attached to the band of a hemostasis device in its intended configuration, such that airflow is all or partially kinked off between the balloons. According to the various method embodiments described herein, one or more pieces of secondary material can optionally be included within each channel to help hold the channel open. These "breather strips" may be one or more additional pieces of material included within the channel, which may be comprised of either air-permeable or air-impermeable materials, and may be of any suitable shape (e.g., a circular or oval cross-sectional). Alternatively, or in addition, the channel(s) can be partially held open along their edge(s) by creating height along the one or more perimeter(s) of the balloon assembly construction using: one or more additional layer(s) of material; a glue line; and/or an extruded bead or weld line resulting from a RF welding process, along the one or more perimeter(s). Various examples of constructing air channel(s) with and without breather strip(s) are shown in FIGS. 11-17 and will be discussed in detail below.

Figure 10:
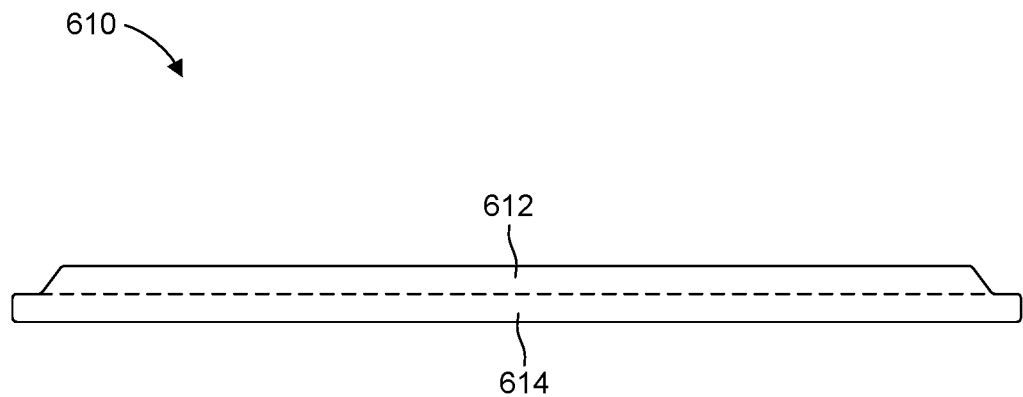
FIG. 10 is a sectional view of a balloon assembly constructed according to a prior art method.

Another drawback with existing methods of constructing two-layer balloon assemblies is resulting expansion defects or failures caused by the top and bottom layers of material adhering to another and failing to properly separate to permit the balloon(s) to inflate after long periods of having been adjacent to another (i.e., after long periods of the balloon(s) being uninflated). Referring now to FIG. 10, a sectional view of a balloon assembly 610 constructed according to a prior art method is shown, in an uninflated state, with a top layer 612 and a bottom layer 614 thereof shown adjacent to another with no air gap or space between the layers 612,614. In this prior art embodiment, the entirety of the two layers 612,614 are adjacent each other, with no gaps or spaces between the two layers 612,614 to assist in separation of the two layers 612,614 as air is introduced into the balloon assembly 610.

In some embodiments according to the present disclosure, this expansion failure is addressed by including spacer(s), strip(s), and/or additional layer(s) of material between the top and bottom layers of the balloon, or otherwise forming space(s) between the layers of material. Materials can be added within formed air channel(s) to prevent these air paths from sealing off when the balloon assembly is folded. These "breather strips" are formed from air-permeable materials, including but not limited to felt, thread, paper, and porous plastic. In alternative embodiments, non-permeable materials can be placed such that they prop open air channel(s), thus allowing air to pass through the channel(s) adjacent to the material. Suitable non-permeable materials include but are not limited to tubing, stickers (adhesive backed paper), flexible sheets of either similar or dissimilar material to the material of the flexible sheet of the balloon, and/or cured glue. Holding channel(s) open at their edges via non-permeable materials, as shown in the examples of FIGS. 11-15 below, achieves the same effect as inserting air-permeable "breather strips" between layers of the balloon to form air channel(s). These space(s) may be located in the vicinity of the air injection port such that when air is injected into the balloon(s) the space serves as a trigger that helps peel apart any adhesions between the layers as air continues to flow into the balloon(s). Breather strips may be of any suitable cross-sectional shape, including but not limited to circular, oval, or rectangular.

Figure 11:
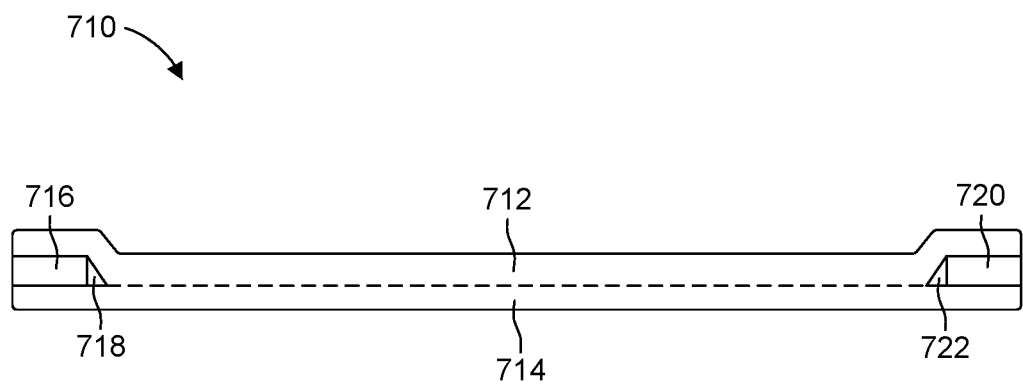
FIG. 11 is a sectional view of a balloon assembly constructed according to a method of the present disclosure.

FIG. 11 shows a sectional view of a balloon assembly 710 constructed according to a method of the present disclosure, in an uninflated state, with a top layer 712 and a bottom layer 714 thereof shown mostly adjacent to another, but further including spacers 716,720 along the side edges (inner periphery) of the balloon assembly 710 that introduce air gaps 718,722 adjacent to the spacers 716,720 such that when air is introduced into the balloon assembly 710 between the top layer 712 and bottom layer 714, the air gaps 718,722 created by the spacers 716,720 serve as air flow paths that promote proper inflation of the balloon assembly 710, overcoming any adherence between the two layers 712,714. In this embodiment, the spacers 716,720 are formed of one or more intermediate layers of material that are placed and welded or bonded between the top layer 712 and bottom layer 714.

Figure 6A:
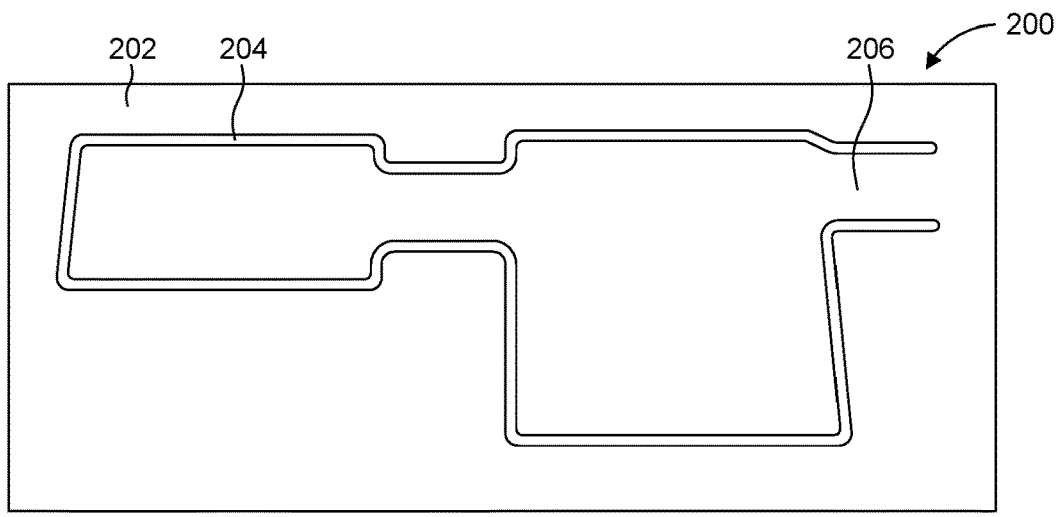
FIGS. 6A-6C show steps of a method of constructing a folded balloon assembly in accordance with the present disclosure.
Figure 6B:
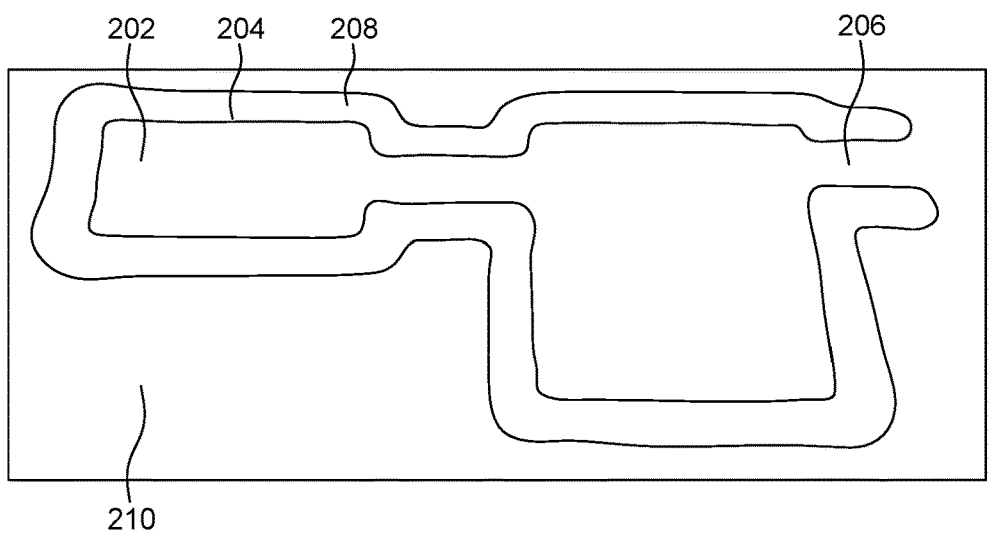
Figure 6C:
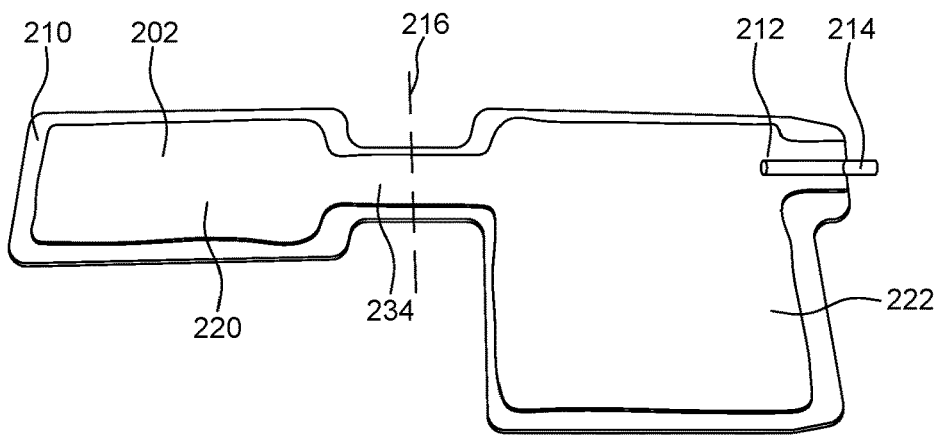

Many materials and methods could be used to create appropriate space between layers of a balloon assembly in order to prevent expansion failures. One method 200 of making a two-layered balloon assembly including appropriate spaces about the edges, as shown in FIGS. 6A-6C above, includes the steps of: (1) depositing a first layer (inner line) of glue 204 on a bottom sheet 202 while leaving a space 206 to form an air inlet 212 (see FIG. 6A); (2) curing the first layer (inner line) of glue 204 to create a perimeter (see FIG. 6A); (3) depositing a second layer (outer line) of glue 208 on the bottom sheet 202 just to the outside of the first layer (inner line) of glue 204 (see FIG. 6B); (4) placing a top sheet 210 on top of the first and second glue layers 204,208 and bottom sheet 202, which results in the uncured second layer (outer line) of glue 208 spreading outwardly away from the first layer (inner line) of glue 204 (see FIG. 6B); (5) inserting a piece of connection tubing 214 into the formed inlet 212 (see FIG. 6C); (6) spreading the glue around the exterior perimeter of the connection tubing 214; (7) curing the second layer (outer line) of glue 208 to completely seal the two layers of material together around the deposited perimeter and inlet 212 (see FIG. 6C); and (8) cutting the sheets 202,210 to form an unfolded balloon assembly (see FIG. 6C). Thus, according to this method, the first layer (inner line) of glue 204 acts to space the bottom sheet 202 and top sheet 210 apart, preventing expansion failures. As shown in FIG. 6C, the constructed balloon assembly can then be folded along fold line 216 to form a two-chambered balloon assembly with a single weld perimeter and no connection port between the balloons. As shown in FIG. 6C, according to this method 200 a balloon assembly comprising a first chamber 220, a second chamber 222, and a channel 234 that connects the first and second chambers 220,222 together in fluid flow communication is formed.

Figure 7A:
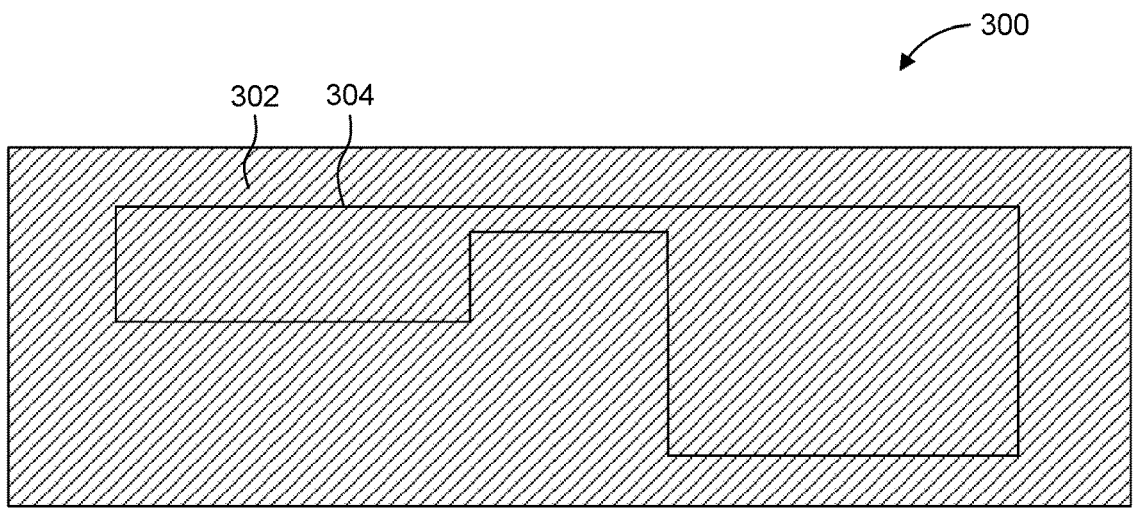
FIGS. 7A-7L show steps of another method of constructing a folded balloon assembly in accordance with the present disclosure.
Figure 7B:
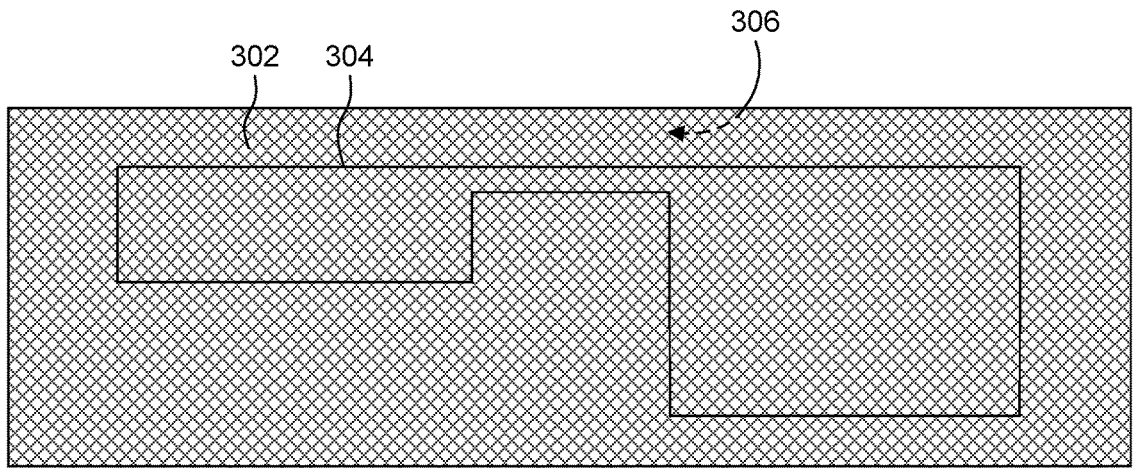
Figure 7C:
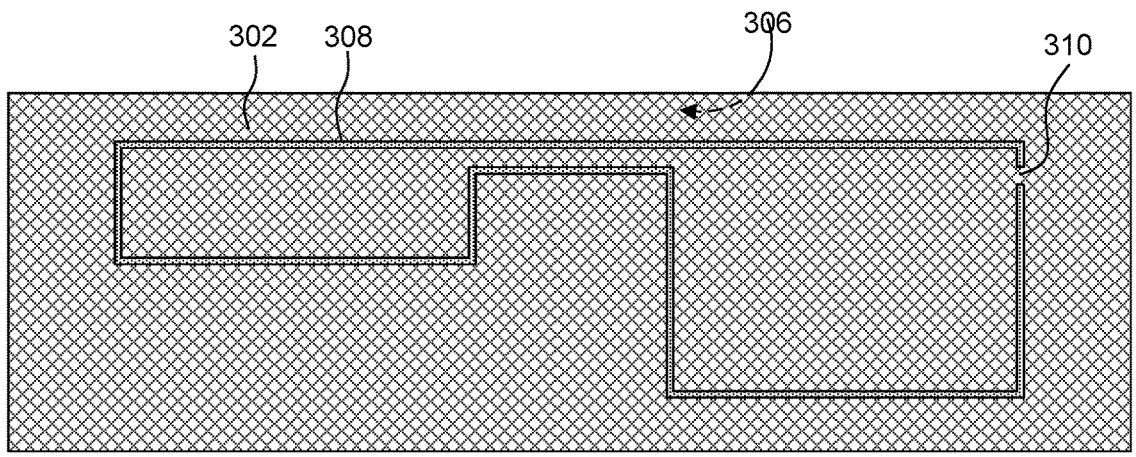
Figure 7D:
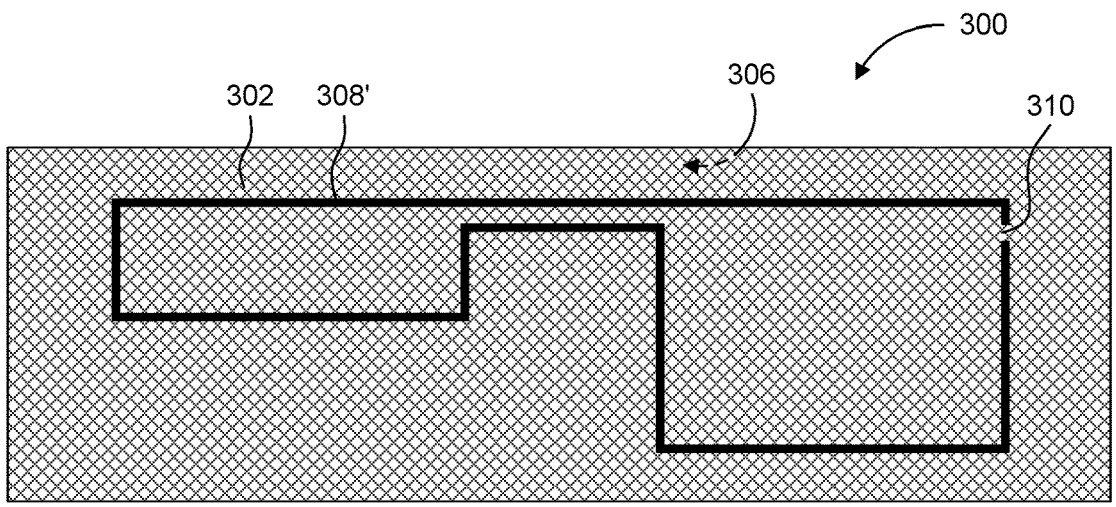
Figure 7E:
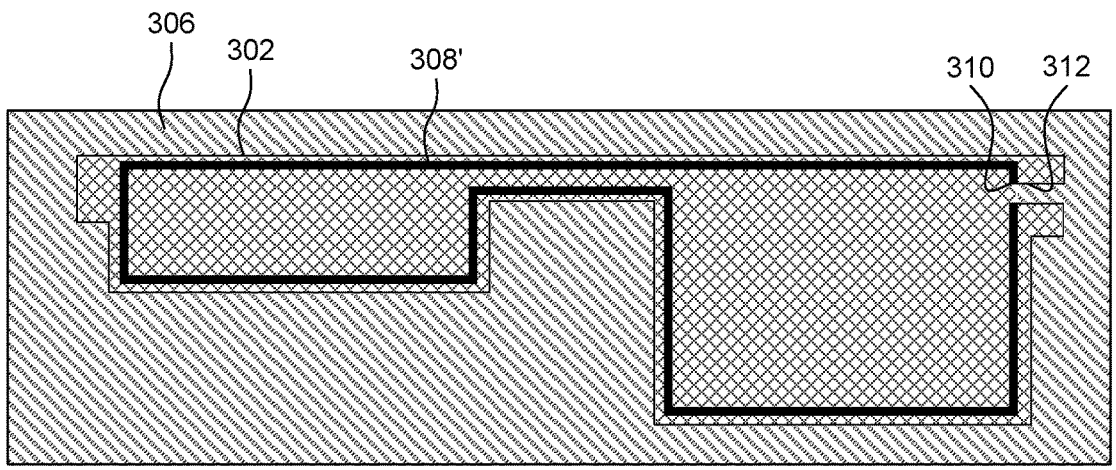
Figure 7F:
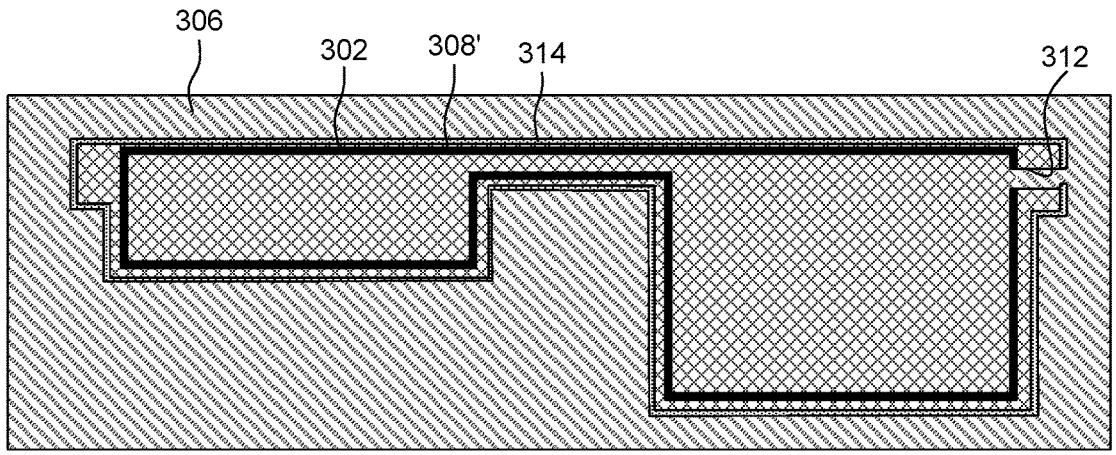
Figure 7G:
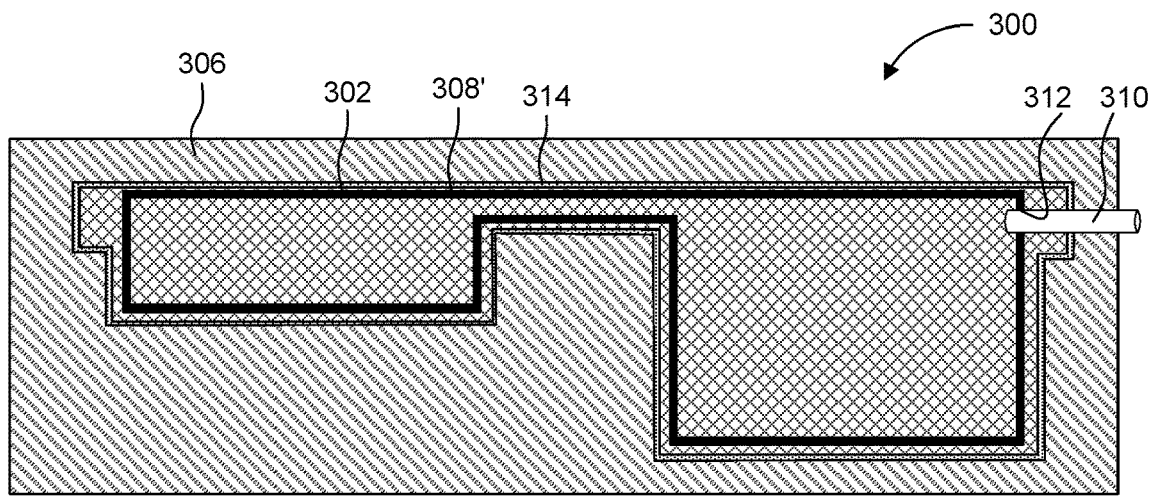
Figure 7H:
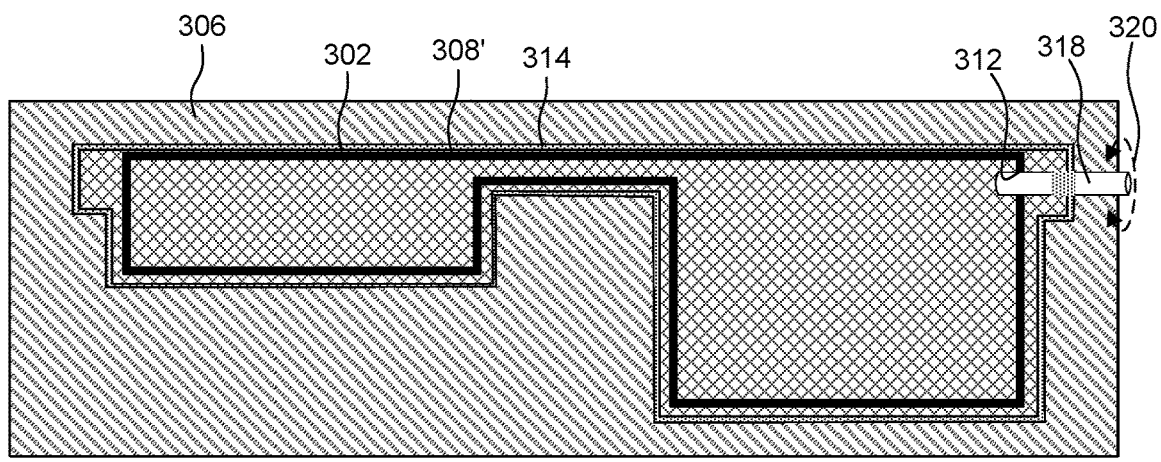
Figure 7I:
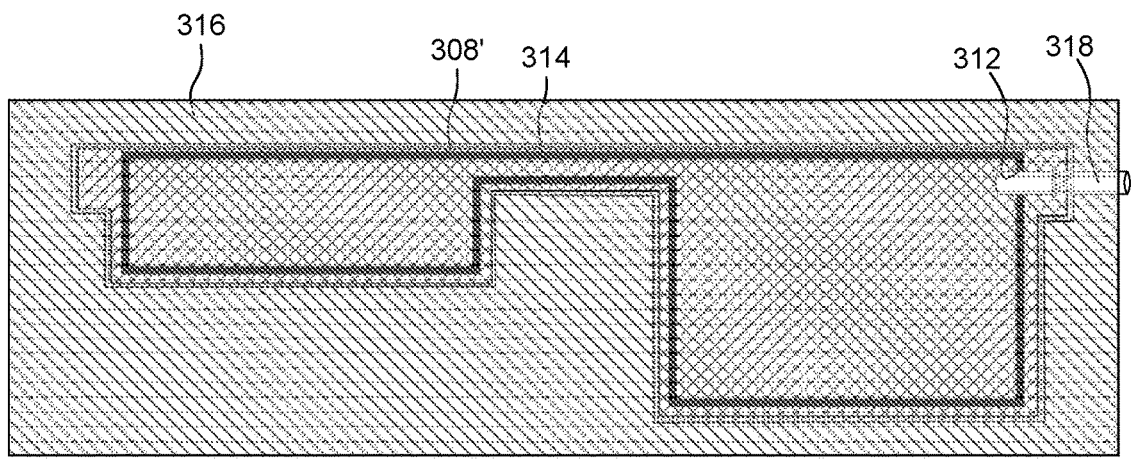
Figure 7J:
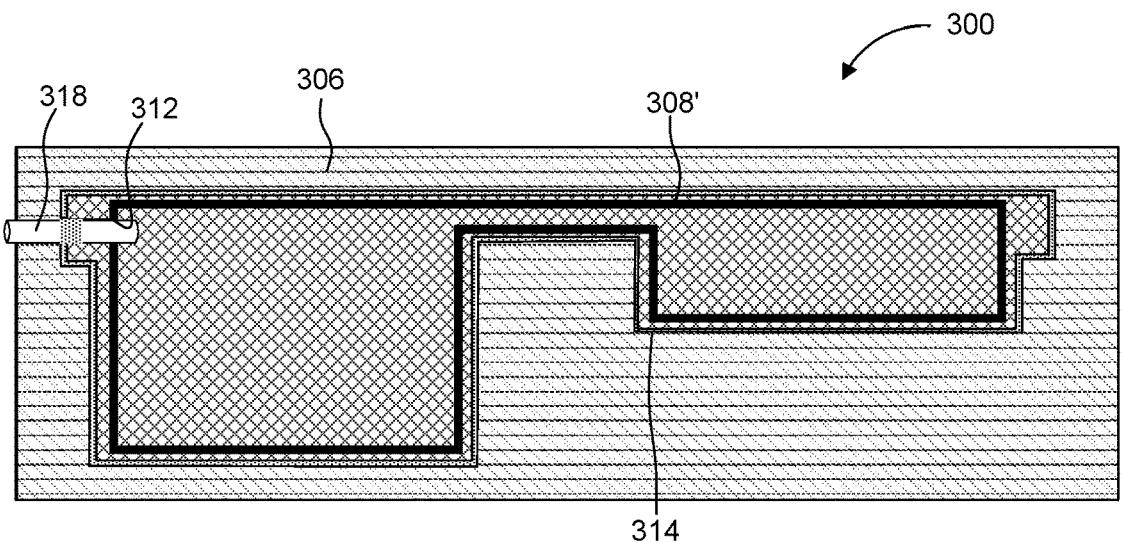
Figure 7K:
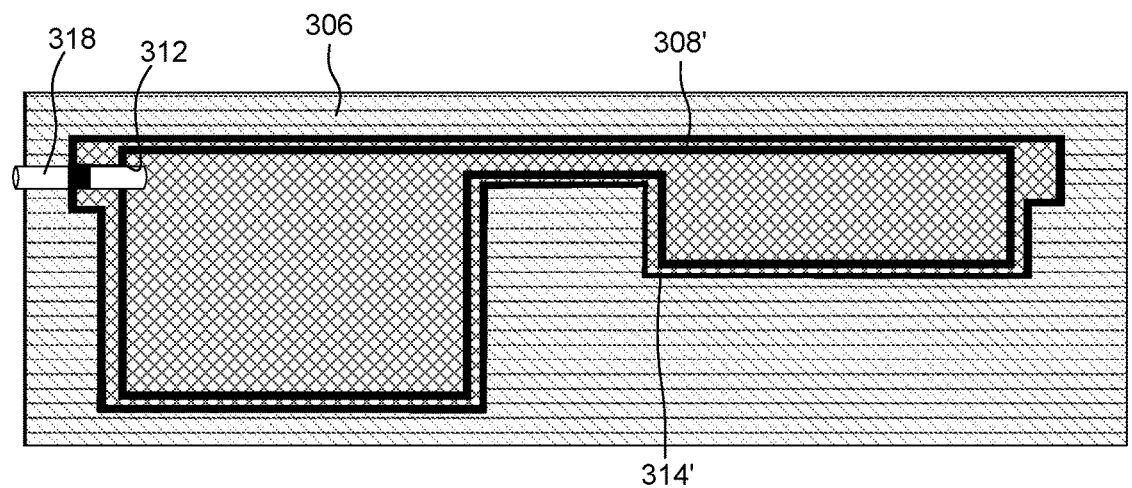

Another method of creating appropriate space between layers of a balloon assembly is to use one or more intermediate layer(s) as spacer(s) between top and bottom layers of a balloon. One such method 300 and apparatus formed thereby is illustrated in FIGS. 7A-7L. In the step shown in FIG. 7A, a middle sheet 302 including an outline 304 for deposition of a glue layer thereon is cut and placed on a worksurface. In the Figures, the middle sheet 302 is schematically indicated by a fill pattern consisting of "upward" diagonal lines angled at 45 degrees from bottom left to top right. In the step shown in FIG. 7B, the middle sheet 302 is placed atop a bottom sheet 306 (which is schematically represented in the Figures by a fill pattern consisting of "downward" diagonal lines angled at 45 degrees from top left to bottom right). In the step shown in FIG. 7C, a first glue layer 308 (e.g., a UV glue) is then applied to the middle sheet 302, following the outline 304 and leaving a space 310. In FIG. 7C, the dotted fill within the first glue layer 308 indicates that the first glue layer 308 is uncured during this step. In the step shown in FIG. 7D, the first glue layer 308 is cured (the solid-fill used in FIGS. 7D-7L is used to indicate the cured first glue layer 308'). In the step shown in FIG. 7E, the middle sheet 302 is cut, leaving a portion of an inlet 312 corresponding with the location of the space 310. In the step shown in FIG. 7F, a second glue layer 314 (e.g., a UV glue) is applied around the perimeter of the cut middle sheet 302, including around the opening of the inlet 312. The dotted fill shown in FIGS. 7F-7J is used to depict that the second glue layer 314 is uncured during these steps. In the step shown in FIG. 7G, a connection tubing 318 is inserted within the inlet 312, and in the step shown in FIG. 7H, the connection tubing 318 is rotated in one or both rotational direction(s) 320 to fully apply the uncured glue of the second glue layer 314 around the connection tubing 318 in the circumferential direction. In the step shown in FIG. 7I, a top sheet 316 is overlaid on top of the middle sheet 302, the top sheet 316 being schematically represented in the figures via a fill pattern consisting of horizontal lines. In the step shown in FIG. 7J, the partial balloon assembly is flipped over so that the glue of the second glue layer 314 is properly applied to the top sheet 316, and in the step shown in FIG. 7K the second glue layer 314 is cured (the cured second glue layer is designated 314' in FIG. 7K and shown with a solid fill in FIGS. 7K and 7L). If necessary, double-sided tape may be used in some of the steps shown in FIGS. 7A-7L, for example: the step shown in FIG. 7B to hold the middle sheet 302 in place atop the bottom sheet 306; and in the step shown in FIG. 7I to hold the connection tubing 318 in place within the inlet 312 before curing of the UV glue.

Figure 7L:
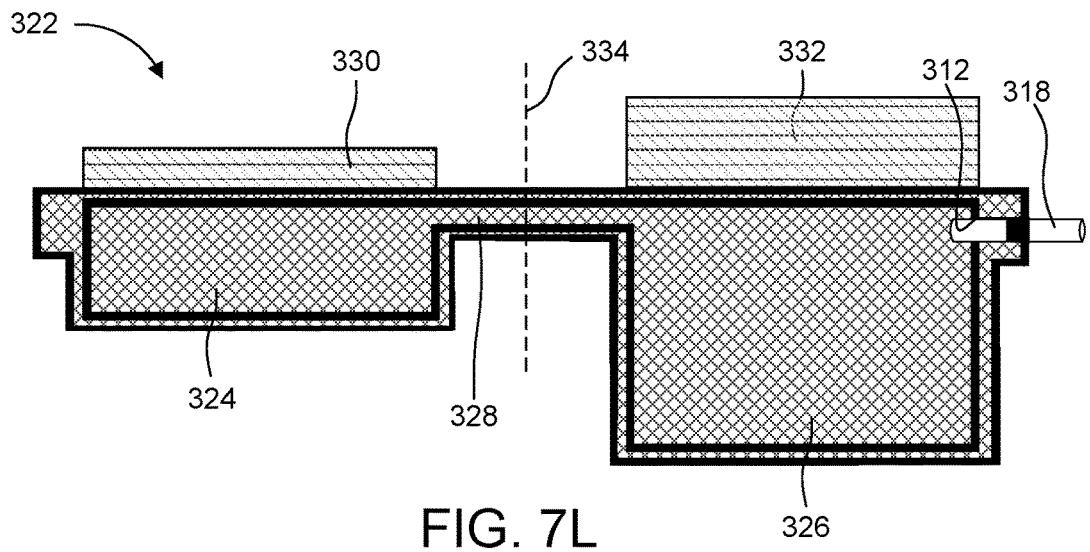

FIG. 7L is a schematic view of an unfolded balloon assembly 322 formed according to the method 300 described above. FIG. 7L clearly shows the formed small balloon 324 and large balloon 326 connected together via an air channel 328 such that introduction of air into the inlet 312 via the connection tubing 318 will inflate both balloons 324,326. In this embodiment, the unfolded balloon assembly 322 includes tabs 330,332 that permit for final assembly of the balloon assembly once it has been folded along fold line 334, and these tabs 330,332 can serve as one or more attachment hinge(s) for connecting the completed balloon assembly to a hemostasis device (e.g., band or other closure device).

Figure 18:
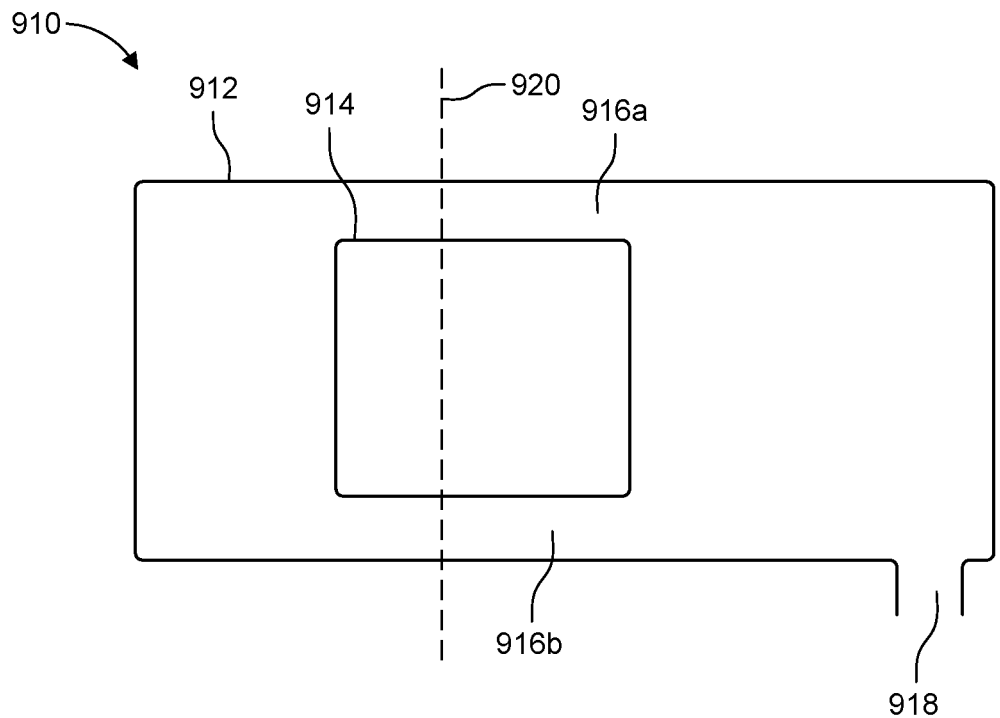
FIGS. 18 and 19 are schematic views of a balloon assembly constructed according to a method of the present disclosure.
Figure 19:
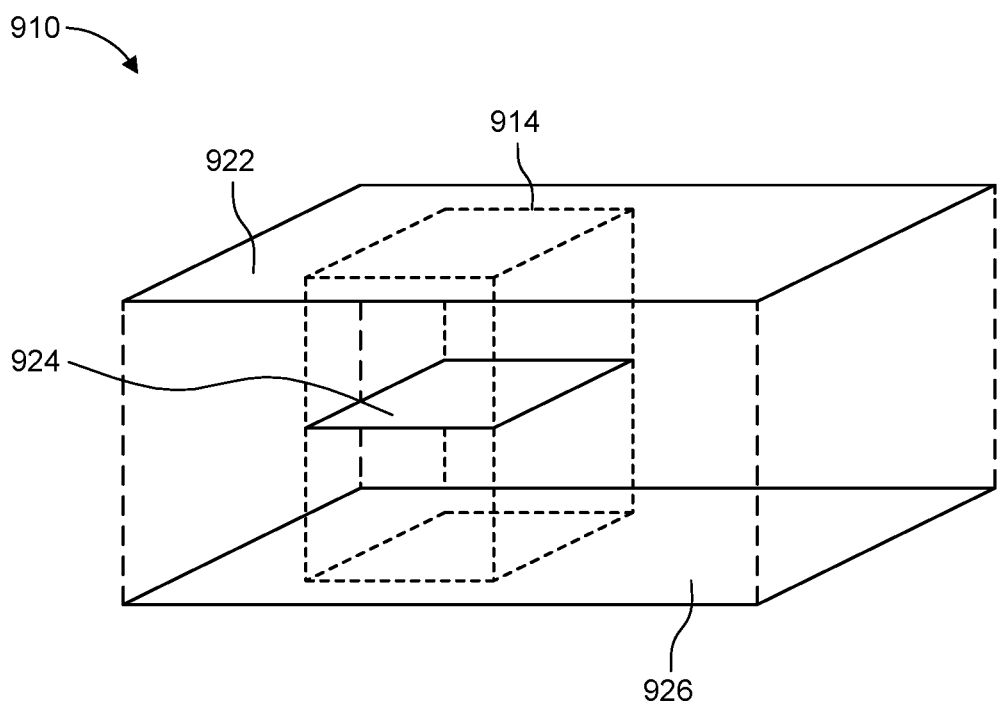

FIGS. 18 and 19 schematically depict a balloon assembly 910 that includes one (or more) intermediate layer(s) used as spacer(s) between top and bottom layers thereof, that has been formed according to another method of the present disclosure. FIG. 18 schematically depicts an unfolded balloon assembly 910 formed by bonding or laser welding a top layer 922, middle layer 924, and bottom layer 926 together via a weld line 912 located around an exterior perimeter of the balloon assembly 910, and a weld line 914 located around an interior perimeter of the balloon assembly 910, with the top layer 922 and bottom layer 926 welded (or bonded) together via the exterior weld line 912 at the perimeter (leaving space 918 for an air inlet), and the middle layer 924 welded (or bonded) to both of the top layer 922 and the bottom layer 926 via weld line 914 to act as a spacer therebetween (the squares projecting upwardly and downwardly from the middle layer 924 in FIG. 19 depict the weld/bonding locations to the respective layers 922,926). The weld line 914 creates a pair of channels 916a,916b on either side thereof, such that when the balloon assembly 910 is folded about fold line 920 to form a completed balloon, air can travel through these channels 916a,916b between the two formed balloon chambers. The balloon assembly 910 of the present embodiment has both two- and three-layer portions, with the three-layer portions acting to prevent expansion failure in the remainder of the balloon assembly 910. In this embodiment, once folded it is possible to cut out the interior area of the center welded area (the area inside weld line 914), since this is not necessary for proper functioning of the balloon assembly 910. By this method, an "end-fold" balloon assembly—similar to the balloon assembly 116 of FIGS. 1-5—is constructed.

FIGS. 8A-8C show steps of yet another method 400 of constructing a balloon assembly in accordance with the present disclosure. It should be understood that the steps of the method 400 are shown schematically in FIGS. 8A-8C, and that certain parts of the structure (e.g., attachment tabs or hinges) are omitted from these figures for simplicity.

FIG. 8A shows the three separate sheets or layers of a balloon assembly 416 that will be constructed, prior to stacking and welding steps. In this embodiment, these layers consist of a bottom sheet 402, a middle sheet 404, and a top sheet 410. The bottom sheet 402 comprises a printed indicator 403 that will be used to assist the clinician in proper alignment of the balloon assembly 416 in relation to a vascular access site where hemostasis is to occur, and the middle sheet 404 comprises a first cutout 406 that creates an outer perimeter of material and a central void and a second cutout 408 that is used to form part of an inlet 418 of the balloon assembly.

FIG. 8B shows a step of the method 400 where the three sheets 402,404,410 are stacked and welded together about an outer perimeter 420 and an inner perimeter 422 to form a welded sheet set 412, prior to cutting. In the step shown in FIG. 8C, the (unfolded) balloon assembly 416 has been formed by cutting the three sheets just exterior to the outer perimeter (weld line) 420, leaving an opening for the inlet 418. In this embodiment the balloon assembly 416 has also been cut just interior to the inner perimeter (weld line) 422 to form an interior cutout 424—as in the embodiment of a balloon assembly 116—though this step may be omitted in alternative embodiments of the method 400.

FIGS. 9A-9H show steps of a method 500 of constructing a hemostasis device including a folded balloon assembly in accordance with the present disclosure. In the step shown in FIG. 9A, an indicator is printed onto a bottom layer 502 of what will become a balloon assembly 516 (see FIG. 9C). In the step shown in FIG. 9B, one or more additional layer(s) of material are laser welded atop the bottom layer 502 such that the indicator 504 is interior to the perimeter of what will become the balloon assembly 516, and a small balloon 520, an attachment tab 542 adjacent to the small balloon 520, a large balloon 522, an attachment tab 540 adjacent to the large balloon 522, and a pair of channels 534a,534b connecting the small balloon 520 and large balloon 522 together are formed. In the step shown in FIG. 9C, the two or more welded layers of material that form the unfolded balloon assembly 516 are die cut around the weld lines to form the separable, unfolded balloon assembly 516 shown. In the step shown in FIG. 9D, the attachment tab 542 that is connected to the small balloon 520 is laser welded to a material layer that will become a band 512 of a hemostasis device. In the step shown in FIG. 9E, the balloon assembly 516 is folded along a fold line 536 so that the large balloon 522 is placed atop the small balloon 520 (i.e., the large balloon 522 overlays the small balloon 520), a first portion of the channel 534a is placed atop a second portion of the channel 534a, and a first portion of the channel 534b is placed atop a second portion of the channel 534b. In the step shown in FIG. 9F, the attachment tab 540 that is connected to the large balloon 522 is laser welded to the band 512. In the step shown in FIG. 9G, complementary fastener patches (e.g., hook-and-loop patches) 513,514 are impulse welded to opposite ends of the band 512. Finally, in the step shown in FIG. 9H, the band 512 is die cut into its final shape, including any comfort-enhancing features (e.g., to include scalloped or otherwise interrupted edges). It should be understood that alternative methods according to the steps discussed above are possible within the scope of the present disclosure, in which the construction method steps or order thereof are modified, as would be appreciated by a person having ordinary skill in the art.

As discussed above, various methods of forming a balloon assembly or air channel(s) thereof that include a breather strip or other gap-creating structure for reducing the risk of adhesion failures are contemplated according to the present disclosure. Each of FIGS. 12-17 show schematic cross-sectional views of various balloon assemblies constructed according to methods of the present disclosure, taken along hypothetical line X-X of FIG. 5, thus showing the cross-sectional area of a channel member for discussion purposes.

Figure 13:
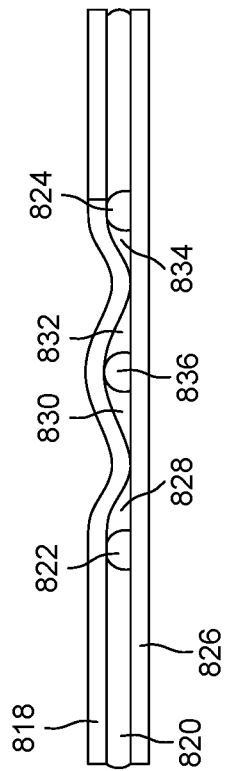
FIGS. 12-17 are schematic cross-sectional views of various balloon assemblies constructed according to methods of the present disclosure, taken along hypothetical line X-X of FIG. 5.
Figure 12:
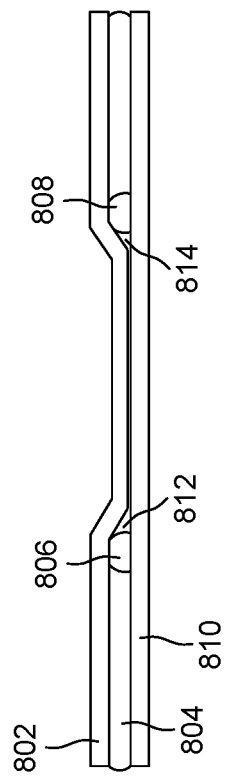

FIG. 12 shows a cross-sectional view of a glued or laser-welded balloon assembly or air channel of three-layer construction, without a breather strip. In this embodiment, the balloon assembly or air channel comprises a top layer 802, a middle layer 804, and a pair of spacers 806,808 in the form of weld or glue lines that are formed at the inner peripheral edges of the middle layer 804 via gluing or a laser welding process. Each of the spacers 806,808 creates a respective gap 812,814 between the top layer 802 and bottom layer 810 through which air can flow, thus reducing the likelihood of adhesion failures. Similarly, FIG. 13 shows a cross-sectional view of a glued or laser-welded balloon assembly or air channel of three-layer construction, but including a breather strip. In this embodiment, the balloon assembly or air channel comprises a top layer 818, a middle layer 820, and a pair of spacers 822,824 in the form of weld or glue lines that are formed at the inner peripheral edges of the middle layer 820 via gluing or a laser welding process. Each of the spacers 822,824 creates a respective gap 828, 834 between the top layer 818 and bottom layer 826 through which air can flow, thus reducing the likelihood of adhesion failures. Further, in this embodiment a breather strip 836 is included within the air channel, thus creating additional gaps 830,832 located on either side of the breather strip 836, further assisting in the reduction of risk of adhesion failure.

Figure 15:
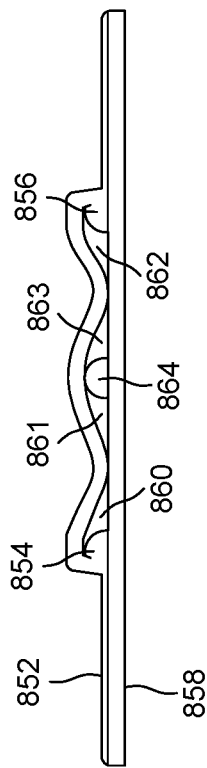
Figure 14:
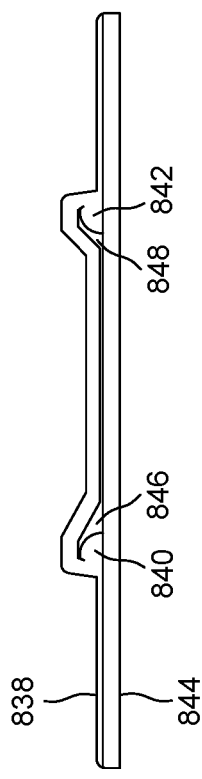

FIG. 14 shows a cross-sectional view of a balloon assembly or air channel of two-layer construction formed via a RF welding process, without a breather strip. In this embodiment, the balloon assembly or air channel comprises a top layer 838 and a bottom layer 844. The RF welding process that is used to attach the top layer 838 to the bottom layer 844 creates a pair of weld lines 840,842, adjacent to each of which respective gaps 846,848 are formed between the top layer 838 and bottom layer 844 through which air can flow, thus reducing the likelihood of adhesion failures. Similarly, FIG. 15 shows a cross-sectional view of a balloon assembly or air channel of two-layer construction formed via a RF welding process, but including a breather strip. In this embodiment, the balloon assembly or air channel comprises a top layer 852 and a bottom layer 858. The RF welding process that is used to attach the top layer 852 to the bottom layer 858 creates a pair of weld lines 854,856, adjacent to each of which respective gaps 860,862 are formed between the top layer 852 and bottom layer 858 through which air can flow, thus reducing the likelihood of adhesion failures. Further, in this embodiment a breather strip 864 is included within the air channel, thus creating additional gaps 861,863 located on either side of the breather strip 864, further assisting in the reduction of risk of adhesion failure.

Figure 17:
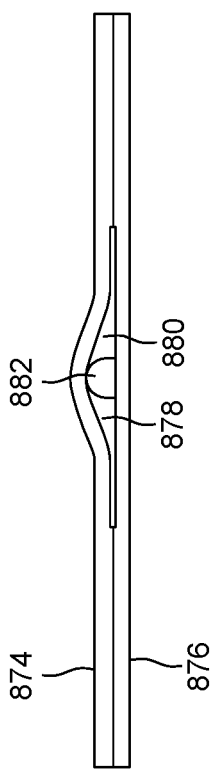
Figure 16:
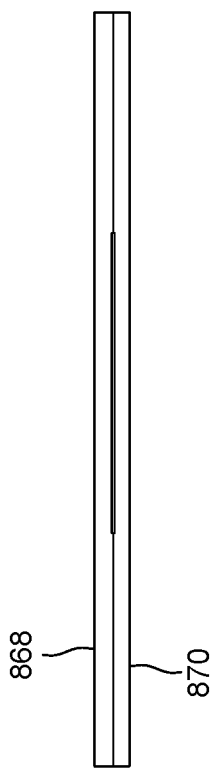

FIG. 16 shows a cross-sectional view of a balloon assembly or air channel of two-layer construction formed via a laser welding process, without a breather strip. In this embodiment, the balloon assembly or air channel comprises a top layer 868 and a bottom layer 870, with no gap between the two layers 868,870 that can help to reduce the risk of adhesion failure between the two layers 868,870. Some balloon assemblies according to the prior art are constructed in this fashion. FIG. 17, on the other hand, shows a cross-sectional view of a balloon assembly or air channel of two-layer construction formed via a laser welding process, but including a breather strip 882 between a top layer 874 and bottom layer 876 of the construction, thus creating gaps 878,880 located on either side of the breather strip 882 that assist in the reduction of risk of adhesion failure.

While the principles of the claimed invention have been described above in connection with specific embodiment(s), it is to be clearly understood that this description is made only by way of example and not as a limitation of the scope of the invention, as set forth in the appended claims.

The invention claimed is:

1. A method of constructing a hemostasis device, the method comprising:
forming a balloon assembly by attaching a top layer of material, a bottom layer of material, and at least one intermediate layer of material together about a perimeter to form at least a portion of a first chamber, at least a portion of a second chamber and at least a portion of at least one channel, the at least one channel being in fluid flow communication between the first chamber and the second chamber, the first chamber and the second chamber being inflatable, the at least one intermediate layer creating a gap between the top layer of material and the bottom layer of material adjacent to the perimeter; and
connecting the balloon assembly to a flexible band that is attachable around a body part of a patient, the flexible band including opposite end portions and an intermediate portion positioned between the opposite end portions; and
the connecting of the balloon assembly to the flexible band including connecting the balloon assembly to the intermediate portion of the flexible band so that the first and second chambers overlie the intermediate portion of the flexible band and so that the opposite end portions of the flexible band extend outwardly beyond opposite ends of the balloon assembly, the hemostasis device having, after the balloon assembly is connected to the flexible band, the first and second chambers in fluid communication with one another by the at least one channel and positioned in overlying relation to one another.

2. The method of claim 1, the forming step further comprising attaching the top layer of material, the bottom layer of material, and the at least one intermediate layer of material together about the perimeter to form the first chamber, the second chamber, and the at least one channel, the first chamber, second chamber, and at least one channel forming a contiguous chamber.

3. The method of claim 2, wherein the connecting of the balloon assembly to the flexible band includes connecting the balloon assembly to the flexible band while the first and second chambers are positioned in overlying relation to one another.

4. The method of claim 1, wherein the forming step further comprises attaching the top layer of material, the bottom layer of material, and the least one intermediate layer of material together about the perimeter such that at least one space is left in the perimeter, the method further comprising attaching at least one port through the at least one space such that a fluid may be introduced into the first chamber via the at least one port.

5. The method of claim 2, further comprising: prior to completion of the forming step, placing at least one piece of secondary material within the at least one channel.

6. The method of claim 5, wherein the step of placing at least one piece of secondary material within the at least one channel comprises placing at least one piece of gas-permeable secondary material within the at least one channel.

7. The method of claim 5, wherein the step of placing at least one piece of secondary material within the at least one channel comprises placing at least one piece of gas-impermeable secondary material within the at least one channel.

8. The method of claim 5, wherein the step of placing at least one piece of secondary material within the at least one channel comprises placing at least one piece of secondary material within the at least one channel which has a circular cross-sectional shape.

9. The method of claim 2, further comprising folding the at least one channel in half.

10. The method of claim 2, wherein the at least one channel is a first air channel, and further comprising forming a second air channel between the first chamber and the second chamber.

11. The method of claim 2, wherein the forming step further comprises attaching the top layer of material, the bottom layer of material, and the at least one intermediate layer of material together about the perimeter to form an outer perimeter, the method further comprising attaching at least the top layer of material and the bottom layer of material together to form an inner perimeter, the inner perimeter being located interior to the outer perimeter.

12. The method of claim 11, further comprising the step of cutting and removing at least a portion of the top layer of material that is located interior to the inner perimeter and at least a portion of the bottom layer of material that is located interior to the inner perimeter.

13. A method of constructing a balloon assembly for a hemostasis device, the method comprising:
 depositing a first layer of glue onto a first layer of material;
 curing the first layer of glue to form a perimeter, the perimeter forming at least a portion of an outline of a first chamber, at least a portion of an outline of a second chamber, and at least a portion of an outline of at least one channel that is connected between the first chamber and the second chamber;
 depositing a second layer of glue onto the first layer of material exterior to the perimeter;
 placing a second layer of material on top of the second layer of glue and the first layer of material; and
 curing the second layer of glue to attach the second layer of material to the first layer of material and form a contiguous chamber comprising the first chamber, the second chamber, and the at least one channel.

14. The method of claim 13, further comprising the step of inserting a first end of a piece of connection tubing into an interior of the contiguous chamber while leaving a second end of the piece of connection tubing exterior to the contiguous chamber.

15. The method of claim 13, further comprising the step of locating at least a portion of the first chamber such that it overlays at least a portion of the second chamber and such that the at least one channel is folded.

16. The method of claim 15, wherein the locating step further comprises folding the at least one channel such that a first portion of the at least one channel overlays a second portion of the at least one channel.

17. A method of constructing a hemostasis device, the method comprising:
 attaching a first layer of material to a second layer of material about a perimeter to produce a balloon structure, the perimeter defining at least a portion of a first chamber, at least a portion of a second chamber, and at least a portion of at least one channel, the at least one channel being in fluid flow communication between the first chamber and the second chamber, the first chamber, second chamber, and at least one channel forming a contiguous chamber; and
 folding the balloon structure such that at least a portion of the first chamber is in overlying relation to at least a portion of the second chamber and such that the at least one channel is folded to produce a balloon assembly; and
 connecting the balloon assembly to a flexible band configured to be attached around a body part of a patient, the connecting of the balloon assembly to the flexible band occurring after the folding of the balloon structure and while the at least the portion of the first chamber is in overlying relation to the at least the portion of the second chamber and while the at least one channel is folded.

18. The method of claim 17, wherein the attaching of the first layer of material to the second layer of material about the perimeter includes leaving a space between the first layer of material and the second layer of material in the perimeter to form an inlet that communicates with the first chamber, the method further comprising connecting connection tubing to the inlet to permit introduction of fluid into the first chamber.

19. The method of claim 17, wherein the attaching step further comprises attaching the first layer of material to the second layer of material about the perimeter such that at least one gap is left in the perimeter, the method further comprising attaching at least one port through the at least one gap such that a fluid may be introduced into the contiguous chamber via the at least one port.

20. The method of claim 17, further comprising: prior to completion of the attaching step, placing at least one piece of secondary material within the at least one channel.

* * * * *